United States Patent [19]

Kagano et al.

[11] Patent Number: 5,298,630

[45] Date of Patent: Mar. 29, 1994

[54] PROCESSES FOR PRODUCING 2-SUBSTITUTED BENZO[B]THIOPHENE

[75] Inventors: Hirokazu Kagano; Hiroshi Goda; Katsuhiko Yoshida; Masahito Nakano, all of Hyogo, Japan

[73] Assignee: Sumitomo Seika Chemicals Co., Ltd., Hyogo, Japan

[21] Appl. No.: 945,084

[22] Filed: Sep. 15, 1992

[30] Foreign Application Priority Data

Jun. 3, 1992 [JP] Japan .................................. 4-142716
Jun. 3, 1992 [JP] Japan .................................. 4-142718

[51] Int. Cl.$^5$ .................. C07C 319/14; C07D 333/70
[52] U.S. Cl. ......................................... 549/57; 568/41
[58] Field of Search ...................... 549/57; 568/67, 68, 568/41

[56] References Cited

U.S. PATENT DOCUMENTS 2,761,873  9/1956  Gregory et al. ..................... 260/516
4,965,379  10/1990  Ikeda et al. ......................... 549/521
5,169,961  12/1992  Dickman et al. ..................... 549/57

OTHER PUBLICATIONS

J. March, "Advanced Organic Chemistry," 2nd ed., p. 374 McGraw-Hill Book Co., New York (1979).
The Merck Index, M. Windholz ed., entry No. 9922, p. 1454, Merck & Co., Inc., Rahway, N.J. (1983).
G. Gokel et al., *Journal of Chemical Education*, "Phase Transfer Catalysis" 55(6), pp. 350–354 (1978).
W. Weber et al., *Journal of Chemical Education*, "Phase Transfer Catalysis," 55(7), pp. 429–433 (1978).
T. Hivota et al., *Heterocycles*, "A Novel Synthesis of Benzofuron and Related Compounds," 26(6), pp. 2717–2725 (1987).
Tetrahedron, vol. 28, pp. 2553–2573, (1972), "Benzo [1] Thieno (2,3-d) Pyridazines-I Etude Des Conditions D'Acces . . . " by Dore et al.
Comptes Rendus, vol. 234, pp. 736–738, (1952), "Recherches sur les α-acylthionaphtenes et leurs derives . . . ", by Martynoff.
Synthetic Communications, vol. 20 (11), pp. 1687–1695, (1990), "A Practical Synthesis of 2-Carbonylbenzo[B]-thiophenes" by Chi-Nung Hsiao et al.
J. Organic Chem., vol. 17, pp. 350–357, (1952), "The Synthesis of Sulfur-Containing Analogs . . . ", by Ng. Ph. Buu-Hoi et al.
Ber., vol. 97(5), pp. 1470–1481, (1964), "Umsetzung schwefelhaltiger Benzaldehyde mit Diazomethan", by Eistert et al.

*Primary Examiner*—Richard L. Raymond
*Attorney, Agent, or Firm*—Jordan and Hamburg

[57] ABSTRACT

A 2-alkylthiobenzaldehyde of general formula (I) is reacted with a halo compound of general formula (II) to produce a 2-substituted benzo[b]thiophene of general formula (III):

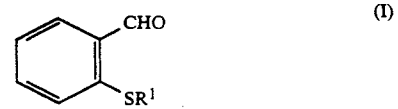

wherein $R^1$ means an alkyl group of 1 to 4 carbon atoms,

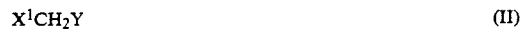

wherein $X^1$ means Cl or Br; Y means $-CO_2H$, $-CO_2R^2$, $-COR^2$, $-CONH_2$ or $-CN$; $R^2$ means an alkyl group of 1 to 4 carbon atoms,

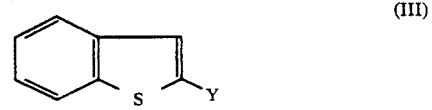

wherein Y is as defined above.

The process of this invention is of great economic and industrial value, for 2-acetylbenzo[b]thiophene and 2-benzo[b]thiophenecarboxylic acid, which are important intermediates for drugs and agricultural chemicals among others, can be obtained in a simple manner, easily and in high yield.

16 Claims, No Drawings

PROCESSES FOR PRODUCING 2-SUBSTITUTED BENZO[B]THIOPHENE

FIELD OF THE INVENTION

The present invention relates to a novel process for producing 2-substituted benzo[b]thiophenes from 2-alkylthiobenzaldehydes.

BACKGROUND OF THE INVENTION

2-Substituted benzo[b]thiophenes are compounds of value as synthetic intermediates for drugs, agricultural chemicals and functional polymers.

The hitherto known production processes for 2-substituted benzo[b]thiophenes, for example 2-acetylbenzo[b]thiophene, are as follows.

(1) The process comprising reacting benzo[b]thiophene with butyllithium and further with N,N-dimethylacetamide

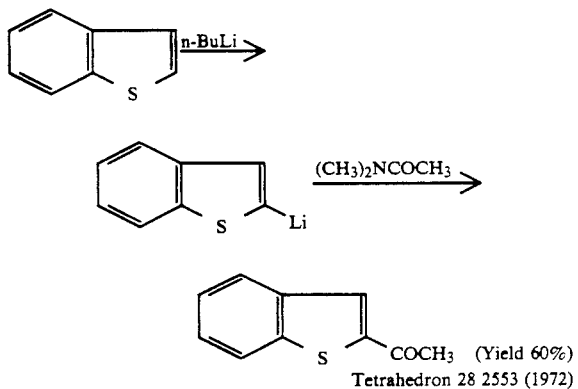

Tetrahedron 28 2553 (1972)

(2) The process comprising reacting sodium salt of 2-mercaptobenzaldehyde with chloroacetone in the presence of sodium hydroxide

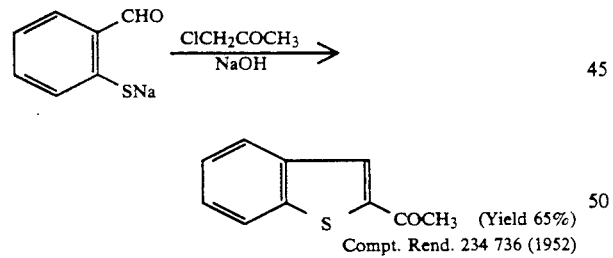

Compt. Rend. 234 736 (1952)

(3) The process comprising reducing thiosalicylic acid with lithium aluminum hydride to lithium salt of 2-mercaptobenzyl alcohol, then reacting it with chloroacetone to give the sulfide and cyclizing the same with pyridine-sulfur trioxide

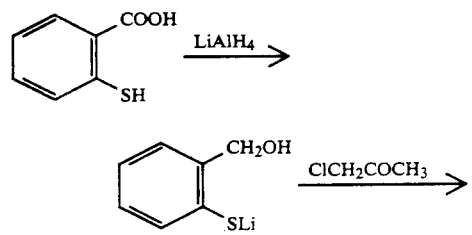

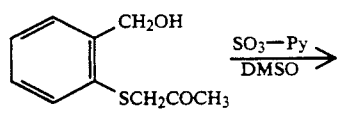

Synthetic Communications 20(11) 1687 (1990)

However, each of these known processes has the following disadvantages.

The process (1) cannot be commercially profitable because of the high cost of the starting material benzo[b]thiophene.

The process (2) has problems in connection with the production of the starting material 2-mercaptobenzaldehyde or corresponding alkali metal mercaptide as well as in the stability of those compounds.

The process (3), like the process (1), involves the use of expensive starting and auxiliary materials and, as such, cannot be commercially profitable.

SUMMARY OF THE INVENTION

Under the circumstances the inventors of the present invention explored in earnest for proposing an expedient and economical process for producing 2-substituted benzo[b]thiophenes. As a result, it was found that when a 2-alkylthiobenzaldehyde of general formula (I) is reacted with a halo compound of general formula (II), there is easily obtained a 2-substituted benzo[b]thiophene of general formula (III) as shown schematically below and that this reaction is accelerated in the presence of a solid base, a solid acid, a solid alkali metal salt or the like. The present invention has been developed on the basis of the above findings.

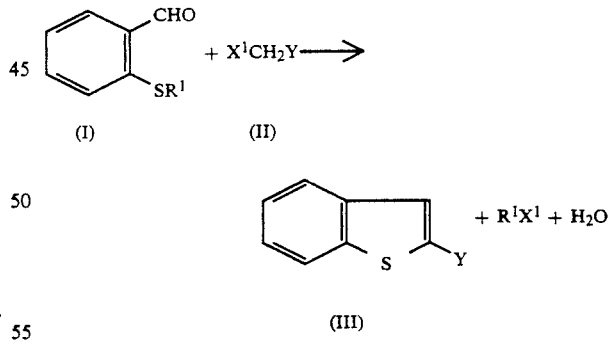

In the above formulas (I), (II) and (III), $R^1$ means an alkyl group containing 1 to 4 carbon atoms; $X^1$ means Cl or Br; Y means $-CO_2H$, $-CO_2R^2$, $-COR^2$, $-CONH_2$ or $-CN$, where $R^2$ is a $C_{1-4}$ alkyl group.

The present invention is, thus, directed to a process for producing a 2-substituted benzo[b]thiophene characterized by reacting an 2-alkylthiobenzaldehyde with a halo compound, if necessary in the presence of a solid base, a solid acid, a solid alkali metal salt or the like.

Referring to the above reaction schema, $R^1$ means a $C_{1-4}$ alkyl group. This alkyl group may be straight-chain or branched. Such alkyl group includes, among others, methyl, ethyl, n-propyl, isopropyl, n-butyl, isobutyl, s-butyl, t-butyl and so on.

The 2-substituted benzo[b]thiophene of general formula (III) according to the invention includes, among others, 2-benzo[b]thiophenecarboxylic acid, methyl 2-benzo[b]thiophenecarboxylate, ethyl 2-benzo-[b]thiophenecarboxylate, 2-acetylbenzo[b]thiophene, 2-propionylbenzo[b]thiophene, 2-benzo[b]thiophenecarboxamide, 2-cyanobenzo[b]thiophene and so on.

The 2-alkylthiobenzaldehyde to be used in the present invention has 1 to 4 carbon atoms in its alkyl moiety and, as such, includes 2-methylthiobenzaldehyde, 2-ethylthiobenzaldehyde, 2-propylthiobenzaldehyde, 2-butylthiobenzaldehyde and so on. Particularly, 2-methylthiobenzaldehyde and 2-ethylthiobenzaldehyde are preferred because of their high reactivity.

The halo compound of general formula (II) includes, among others, chloroacetic acid, bromoacetic acid, methyl chloroacetate, ethyl chloroacetate, chloroacetone, bromoacetone, 1-chloro-2-butanone, chloroacetamide, chloroacetonitrile and so on. The proportion of the halo compound used is generally 0.8 to 10.0 mol equivalents and preferably 1.0 to 6.0 mol equivalents based on 2-alkylthiobenzaldehyde. If the proportion of the halo compound is less than 0.8 mol equivalents, the amount of unreacted 2-alkylthiobenzaldehyde will be increased. On the other hand, the use of the halo compound in excess of 10.0 mol equivalents will not be rewarded with a commensurate effect and, therefore, is uneconomical.

The solid base, solid acid, solid alkali metal salt, perhalic acid and alkali metal salt thereof or the like which is optionally employed in the present invention is not critical in kind. The following is a partial list of such substances in each category.

(1) Solid base: Sodium carbonate, potassium carbonate, calcium carbonate, barium carbonate, sodium tungstate, calcium oxide, magnesium oxide, alumina, anion exchange resins, etc.

(2) Solid acid: Boric acid, boric anhydride, calcium hydrogen phosphate, ferric chloride, aluminum chloride, ferric oxide, silica-alumina, cation exchange resins, zeolite, montmorillonite, etc.

(3) Solid alkali metal salt: Potassium iodide, sodium iodide, potassium bromide, sodium bromide, etc.

(4) Perhalic acid and alkali metal salt thereof: Potassium periodate, sodium periodate, periodic acid, potassium perchlorate, sodium perchlorate, perchloric acid, etc.

From the standpoint of reaction velocity and economy, calcium oxide, magnesium oxide, zeolite, potassium iodide, etc. are preferred. The proportion of said solid base, solid acid, solid alkali metal salt, perhalic acid, alkali metal salt of perhalic acid, etc. used relative to the weight of 2-alkylthiobenzaldehyde is generally 0.005 to 2.0 times and preferably 0.01 to 1.2 times. If the proportion of said solid base, solid acid, solid alkali metal salt, perhalic acid, alkali metal salt of perhalic acid, or the like is less than 0.005 times, the effect of addition will not be appreciable, while the use in excess of 2.0 times will not be rewarded with a commensurate effect and, therefore, is uneconomical.

The reaction of the present invention can be conducted in the presence of a solvent or in the absence thereof. The solvent is not limited in kind. For example, water, hydrocarbons such as n-hexane, n-heptane, cyclohexane, methylcyclohexane, benzene, toluene, xylene, etc., halogenated hydrocarbons such as methylene chloride, 1,2-dichloroethane, chloroform, chlorobenzene, etc., ethers such as ethyl ether, tetrahydrofuran, dioxane, etc., and polar solvents such as N-methyl-2-pyrrolidone, N,N-dimethylformamide, N,N-dimethylacetamide, dimethyl sulfoxide, etc., as well as mixtures thereof, can be mentioned. However, from the standpoint of reaction velocity, the reaction is preferably conducted in the absence of a solvent. The halo compound of general formula (II), which is a reactant, may also be used as the solvent as well.

The reaction temperature is generally 10° to 150° C. and preferably 20° to 130° C. If the reaction temperature exceeds 150° C., side reactions tend to take place. If the temperature is below 10° C., the reaction proceeds only too slowly, thus being undesirable for practical purposes. The reaction time is dependent on the reaction temperature, the presence or absence of said solid base, solid acid, solid alkali metal salt, perhalic acid, alkali metal salt of perhalic acid or the like, species of the same, species of reaction solvent and other factors but is generally within the range of 1 to 50 hours. Isolation of the resulting 2-substituted benzo-[b]thiophene from the reaction mixture can be generally accomplished by diluting the reaction mixture with water, extracting it with an organic solvent and subjecting the extract to crystallization or distillation or by adding an organic solvent to the reaction mixture, removing the insoluble matter by filtration and subjecting the filtrate to crystallization or distillation, to mention but a few procedures.

The production process for 2-substituted benzo[b]thiophenes according to the present invention is economically and industrially advantageous because 2-acetylbenzo[b]thiophene, 2-benzo[b]thiophenecarboxylic acid, etc., which are important intermediates for the production of drugs and agricultural chemicals, can be produced from 2-alkylthiobenzaldehydes expediently, easily and in high yield.

There have been known several processes for the production of alkylthiobenzaldehydes hitherto. Among them are:

(A) The process starting with 4-chlorobenzaldehyde

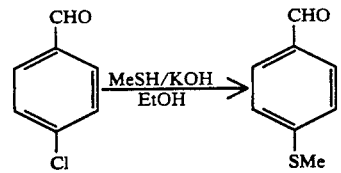

(Yield not mentioned) U.S. Pat. No. 2761873 (1956)

(B) The process starting with thioanisole

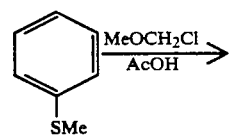

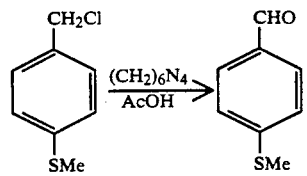

(Yield 21%) J. Org. Chem. 17, 350~7 (1952)

(C) The process starting with 2-methylthiobenzoic acid

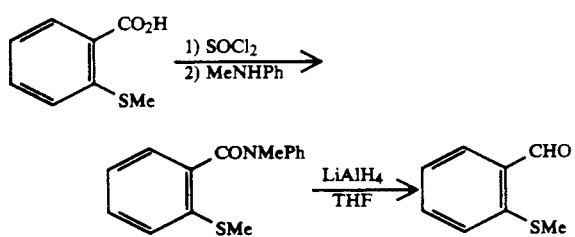

(Yield 51%) Ber. 97(5), 1470~81 (1964)

These known production processes for alkylthiobenzaldehydes have the following disadvantages, though. Thus, according to the check experiment carried out by the inventors of the present invention, the process (A) is disadvantageous in that as chlorobenzaldehyde is reacted with an alkanethiol in a homogeneous system, the alkanethiol tends to react with the active aldehyde group of chlorobenzaldehyde to give by-products so that the yield of the object alkylthiobenzaldehyde is inevitably very low. The processes (B) and (C) have the disadvantages of high material costs, many steps required and low yields and cannot be regarded as commercially profitable processes.

In view of this situation, the inventors of the present invention explored in earnest for proposing a process for producing alkylthiobenzaldehydes in an expedient and economical manner. As a result, they discovered that when a halobenzaldehyde of general formula (IV) is reacted with an alkanethiol of general formula (V) in the presence of a base and water in a heterogeneous phase as schematically shown below, the corresponding alkylthiobenzaldehyde of general formula (VI) is successfully obtained. The present invention has been developed on the basis of the above finding.

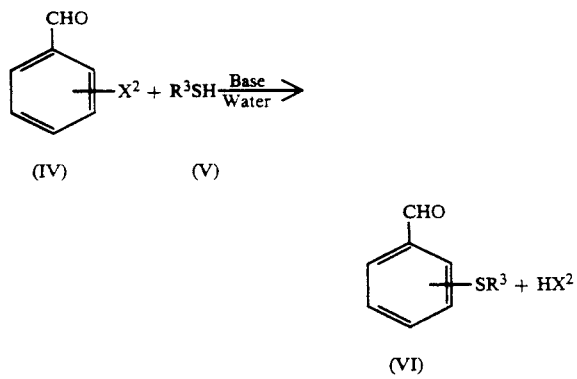

In the above formulas, $X^2$ means Cl or Br; $R^3$ means an alkyl group of 1 to 4 carbon atoms.

Further, the present invention is, therefore, directed to a process for producing an alkylthiobenzaldehyde characterized in that a halobenzaldehyde is reacted with an alkanethiol in the presence of a base and water in a heterogeneous phase. The outstanding feature of this production process for alkylthiobenzaldehydes according to the invention is that the object compounds can be produced starting with halobenzaldehydes, which are commercially available at low can be produced, easily and under comparatively mild conditions.

Referring to the above general formulas (V) and (VI), $R^3$ means an alkyl group containing 1 to 4 carbon atoms. This alkyl group may be straight-chain or branched. Such alkyl group includes, among others, methyl, ethyl, n-propyl, isopropyl, n-butyl, isobutyl, s-butyl, t-butyl and so on.

The alkylthiobenzaldehyde of general formula (VI) includes, among others, 2-methylthiobenzaldehyde, 4-methylthiobenzaldehyde, 2-ethylthiobenzaldehyde, 4-ethylthiobenzaldehyde, 2-n-propylthiobenzaldehyde, 4-n-propylthiobenzaldehyde, 2-isopropylthiobenzaldehyde, 4-isopropylthiobenzaldehyde, 2-n-butylthiobenzaldehyde, 4-n-butylthiobenzaldehyde and so on.

The halobenzaldehyde which is used as a starting material in the present invention includes, among others, 2-chlorobenzaldehyde, 2-bromobenzaldehyde, 4-chlorobenzaldehyde, 4-bromobenzaldehyde and so on.

The alkanethiol which can be used includes, among others, methanethiol, ethanethiol, 1-propanethiol, 2-propanethiol, 1-butanethiol, 2-butanethiol and so on. The proportion of the alkanethiol used is generally 0.8 to 3.0 mol equivalents and preferably 1.0 to 2.0 mol equivalents relative to the halobenzaldehyde. If the proportion of said alkanethiol is less than 0.8 mol equivalents, a substantial amount of the halobenzaldehyde will remain unreacted, while the use of more than 3.0 mol equivalents will be uneconomical because it will not be rewarded with a commensurate effect.

The base which is used in the reaction of halobenzaldehyde with alkanethiol includes, among others, alkali metal hydroxides such as sodium hydroxide, potassium hydroxide, etc., alkali metal carbonates such as sodium carbonate, potassium carbonate, etc., and metal alkoxides such as sodium methoxide, sodium ethoxide and so on. From economic points of view, the use of sodium hydroxide is preferred. The proportion of the base used is generally 0.8 to 3.5 mol equivalents and preferably 1.0 to 2.5 mol equivalents relative to halobenzaldehyde. If the proportion of the base used is less than 0.8 mol equivalents, a substantial amount of the halobenzaldehyde will remain unreacted, while the use of more than 3.5 mol equivalents will not produce a commensurate effect and is, therefore, uneconomical.

The production process for alkylthiobenzaldehydes according to the present invention is characterized in that the reaction is carried out in the presence of water and, hence, in a heterogeneous phase. Thus, because the halobenzaldehyde is water-insoluble, the reaction of halobenzaldehyde with alkanethiol becomes a reaction in a heterogeneous phase. Under the conditions, the addition of a phase transfer catalyst is preferred because the reaction then proceeds more smoothly.

The phase transfer catalyst that can be used for this purpose includes, among others, quaternary ammonium salts such as benzyltriethylammonium bromide, benzyltrimethylammonium chloride, hexadecyltriethylammonium bromide, hexadecyltrimethylammonium chloride, dodecyltriethylammonium chloride, octyltriethylammonium bromide, tetra-n-butylammonium bromide, tetra-n-butylammonium chloride, tetraethylammonium chloride, trioctylmethylammonium chloride, etc., quaternary phosphonium salts such as hexadecyltriethylphosphonium bromide, hexadeccyltributylphosphonium chloride, tetra-n-butylphosphonium bromide, tetra-n-butylphosphonium chloride, trioctylethylphosphonium bromide, tetraphenylphosphonium bromide, etc., and crown ethers such as 18-crown-6, dibenzo-18-crown-6, dicyclohexyl-18-crown-6 and so on. From economic points of view, the use of a quaternary ammonium salt, such as tetra-n-butylammonium bromide, tetra-n-butylammonium chloride, etc., or a quaternary phosphonium salt, such as tetra-n-butylphosphonium bromide, tetra-n-butylphosphonium chloride, etc. is preferred. The amount of the phase transfer catalyst, if used, is generally 0.005 to 0.5 part by weight and preferably 0.01 to 0.2 part by weight to each part by weight of halobenzaldehyde. If the amount of the phase transfer catalyst is less than 0.005 part by weight, the catalytic effect will not be sufficient. On the other hand, the use of more than 0.5 part by weight will not be rewarded with a commensurate effect and be, therefore, uneconomical.

The solvent for the reaction of the present invention may be water alone. However, in order to facilitate progress of the reaction and separation of the reaction product after the reaction, a mixed solvent composed of 1 part by weight of water and 0.1 to 10 parts by weight of a water-insoluble organic solvent can be employed. The water-insoluble organic solvent is not critical in kind and may for example be selected from among hydrocarbons such as n-hexane, n-heptane, cyclohexane, methylcyclohexane, benzene, toluene, xylene, etc. and halogenated hydrocarbons such as methylene chloride, 1,2-dichloroethane, chloroform, chlorobenzene and so on. The proportion of the solvent is generally 1 to 30 parts by weight to each part by weight of the halobenzaldehyde.

The reaction temperature is generally 0° to 150° C. and preferably 20° to 120° C. If the reaction temperature exceeds 150° C., side reactions tend to take place. On the other hand, if the temperature is less than 0° C., the reaction proceeds only too slowly, thus being undesirable for practical purposes. The reaction time is dependent on the reaction temperature, species of phase transfer catalyst and reaction solvent, etc. and cannot be stated in general terms but is generally in the range of 1 to 40 hours.

The alkylthiobenzaldehyde thus produced can be isolated and purified by the conventional procedure such as extraction and distillation. Since the water phase is separated as containing the phase transfer catalyst, it can be recycled for reuse. This means that there is substantially no aqueous effluent problem.

In accordance with the present invention, alkylthiobenzaldehydes can be easily synthesized from halobenzaldehydes, which are commercially available at low prices, by reacting them with an alkanethiol in the presence of a base and water in a heterogeneous phase.

Since the object alkylthiobenzaldehyde can be obtained in such a simple manner with a minimum of waste or effluent to be disposed of and in high yield, the present invention is considered to be of great value both economically and commercially.

The 2-alkylthiobenzaldehyde obtained by the above method, by reacting a 2-halobenzaldehyde with an alkanethiol, can be used profitably as a starting material for 2-substituted benzo[b]thiophene of the general formula (III) as mentioned before.

DETAILED DESCRIPTION OF THE PREFERRED EMBODIMENTS

The following examples are intended to describe the present invention in further detail and should by no means be construed as defining the entire scope of the invention.

EXAMPLE 1

Synthesis of 2-Methylthiobenzaldehyde

A four-necked flask of 200 ml capacity, equipped with a stirrer, thermometer and reflux condensor, was charged with 11.2 g (0.28 mol) of sodium hydroxide and 80 g of water under a nitrogen atmosphere and 13.5 g (0.28 mol) of methanethiol was bubbled through the charge at room temperature for about 1 hour to prepare an aqueous solution of methanethiol sodium salt. To this aqueous solution was added 28.1 g (0.2 mol) of 2-chlorobenzaldehyde and the reaction was conducted in the presence of 1.1 g of tetra-n-butylammonium bromide (phase transfer catalyst) at 80° C. for 4 hours. The reaction mixture was then cooled to room temperature and extracted with methylene chloride. The methylene chloride layer was separated, concentrated and distilled under reduced pressure to give 28.9 g of 2-methylthiobenzaldehyde (b.p. 116°–118° C./5 mmHg). The yield based on 2-chlorobenzaldehyde was 95%.

EXAMPLES 2 to 4

Synthesis of 2-Methylthiobenzaldehyde

The procedure of Example 1 was repeated except that the reaction conditions (temperature and time) and the species of solvent and phase transfer catalyst were changed as shown in Table 1. The results are shown in Table 1.

TABLE 1

|  | Solvent | Phase transfer catalyst | Temperature (°C.) | Time (Hr) | Yield (%) |
|---|---|---|---|---|---|
| Example 2 | H₂O | (n-Bu)₄NCl | 100 | 1 | 93 |
| Example 3 | Toluene—H₂O* | (n-Bu)₄NBr | 90 | 3 | 95 |
| Example 4 | Toluene—H₂O* | (n-Bu)₄PBr | 50 | 14 | 94 |

*Toluene—H₂O is a 1:1 (by weight) mixture.

EXAMPLES 5 to 10

Synthesis of Alkylthiobenzaldehydes

The procedure of Example 1 was repeated except that the halobenzaldehydes and alkanethiols shown in Table 2 were employed. The results are shown in Table 2.

TABLE 2

|  | Halobenzaldehyde | Alkanethiol | Alkylthiobenzaldehyde (b.p.) | Yield (%) |
|---|---|---|---|---|
| Example 5 | 2-Chlorobenzaldehyde | Ethanethiol | 2-Ethylthiobenzaldehyde (131–132° C./5 mm Hg) | 92 |
| Example 6 | 2-Bromobenzaldehyde | 2-Propanethiol | 2-Isopropylthiobenzaldehyde 105–106° C./3 mm Hg) | 90 |
| Example 7 | 4-Chlorobenzaldehyde | Methanethiol | 4-Methylthiobenzaldehyde (128–129° C./5 mm Hg) | 96 |
| Example 8 | 4-Chlorobenzaldehyde | Ethanethiol | 4-Ethylthiobenzaldehyde (130–131° C./5 mm Hg) | 93 |
| Example 9 | 4-Chlorobenzaldehyde | 1-Propanethiol | 4-n-Propylthiobenzaldehyde (139–140° C./ | 89 |

TABLE 2-continued

| | Halobenz-aldehyde | Alkanethiol | Alkylthiobenz-aldehyde (b.p.) | Yield (%) |
|---|---|---|---|---|
| Example 10 | 4-Chlorobenzaldehyde | 1-Butanethiol | 5 mm Hg) 4-n-Butylthiobenzaldehyde (148–149° C./ 5 mm Hg) | 87 |

COMPARATIVE EXAMPLE 1

A four-necked flask (200 ml capacity) equipped with a stirrer, thermometer and condenser was charged with 7.3 g (0.11 mol) of 85% potassium hydroxide and 75 g of ethanol under a nitrogen atmosphere and, then, 5.3 g (0.11 mol) of methanethiol was bubbled through the charge at room temperature for about 1 hour to prepare a solution of methanethiol potassium salt. To this solution was added 14.1 g (0.10 mol) of 2-chlorobenzaldehyde and the reaction was conducted in this homogenous system at 60° C. for 3 hours. After completion of the reaction, the reaction mixture was analyzed by high performance liquid chromatography. The yield of the product 2-methylthiobenzaldehyde based on 2-chlorobenzaldehyde was less than 1%.

EXAMPLE 11

Synthesis of 2-acetylbenzo[b]thiophene

A four-necked flask of 300 ml capacity, equipped with a stirrer, thermometer and condenser, was charged with 30.4 g (0.20 mol) of the 2-methylthiobenzaldehyde obtained by the same way as in Example 1, 27.8 g (0.30 mol) of chloroacetone and 1.52 g of calcium oxide (solid base). The reaction was conducted with stirring at 110° C. for about 2 hours. After completion of the reaction, 150 g of cyclohexane was added and heated. After dissolution, the insoluble matter was removed by filtration while keeping it hot, then the filtrate was cooled for crystallization. The precipitate was collected by filtration and dried to give 32.8 g of 2-acetylbenzo[b]thiophene as light yellow crystals. The yield based on 2-methylthiobenzaldehyde was 93.2%.

EXAMPLES 12–15

Synthesis of 2-Acetylbenzo[b]thiophene

The reaction procedure of Example 11 was repeated except that the additive/amount, mol ratio of chloroacetone and reaction conditions (temperature and time) were varied as shown in Table 3. The results are shown in Table 3.

TABLE 3

| | Additive/amount | (wt. %)[1] | Mol ratio[2] | Temperature (°C.) | Time (Hr) | Yield (%) |
|---|---|---|---|---|---|---|
| Example 12 | None | — | 4 | 120 | 19 | 62 |
| Example 13 | Solid alkali metal salt KI | 80 | 1.2 | 50 | 14 | 74 |
| Example 14 | Solid acid MS-4A[3] | 100 | 4 | 120 | 8 | 81 |
| Example 15 | Solid base MgO | 3 | 6 | 110 | 4 | 90 |

[1] Amount (wt. %): weight % based on 2-methylthiobenzaldehyde
[2] Mol ratio: Mol ratio of chloroacetone to 2-methylthiobenzaldehyde
[3] MS-4A: Zeolite Molecular Sieve 4A

EXAMPLES 16–21

Synthesis of 2-Substituted Benzo[b]thiophenes

The procedure of Example 11 was repeated except that the species of 2-alkylthiobenzaldehyde [$R^1$ in general formula (I)] and halo compound [general formula (II)] were varied as shown in Table 4 to give the corresponding 2-substituted benzo[b]thiophenes [Y in general formula (III)]. The results are shown in Table 4.

TABLE 4

| | $R^1$ in general formula (I) | General formula (II) | Y in general formula (III) | Yield (%)* |
|---|---|---|---|---|
| Example 16 | —$C_2H_5$ | $ClCH_2COCH_3$ | —$COCH_3$ | 92 |
| Example 17 | —$CH_3$ | $ClCH_2CO_2H$ | —$CO_2H$ | 95 |
| Example 18 | —$C_2H_5$ | $BrCH_2CO_2H$ | —$CO_2H$ | 94 |
| Example 19 | —$CH_3$ | $ClCH_2CO_2CH_3$ | —$CO_2CH_3$ | 90 |
| Example 20 | —$CH_3$ | $ClCH_2CONH_2$ | —$CONH_2$ | 87 |
| Example 21 | —$CH_3$ | $ClCH_2CN$ | —$CN$ | 85 |

*Yield (%): The yield of each 2-substituted benzo[b]thiophene of general formula (III) based on the corresponding 2-alkylthiobenzaldehyde of general formula (I)

EXAMPLE 22

Synthesis of 2-Benzo[b]thiophenecarboxylic Acid

A four-necked flask (300 ml capacity) equipped with a stirrer, thermometer and condenser was charged with 30.4 g (0.20 mol) of 2-methylthiobenzaldehyde and 28.4 g (0.30 mol) of monochloroacetic acid and the reaction was conducted with stirring at 110° C. for about 10 hours. After completion of the reaction, 150 g of toluene was added to dissolve the reaction mixture and the solution was cooled for precipitation. The precipitate was collected by filtration and dried to give 28.5 g (yield 80%) of 2-benzo[b]thiophenecarboxylic acid as light yellow crystals.

What is claimed is:

1. A process for producing a 2-substituted benzo[b]thiophene of general formula (III) which comprises reacting an 2-alkylthiobenzaldehyde of general formula (I) with a halo compound of general formula (II):

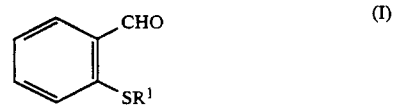

(I)

wherein $R^1$ means an alkyl group of 1 to 4 carbon atoms,

(II)

wherein $X^1$ means Cl or Br; Y means —$CO_2H$, —$CO_2R^2$, —$COR^2$, —$CONH_2$ or —$CN$; $R^2$ means an alkyl group of 1 to 4 carbon atoms,

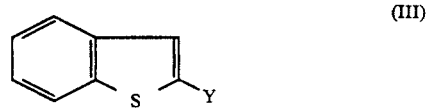

(III)

wherein Y is as defined above.

2. A process according to claim 1 wherein the reaction is conducted in the presence of a solid base.

3. A process according to claim 2 wherein said solid base is calcium oxide or magnesium oxide.

4. A process according to claim 1 wherein the reaction is conducted in the presence of a solid acid.

5. A process according to claim 4 wherein said solid acid is a zeolite.

6. A process according to claim 1 wherein the reaction is conducted in the presence of a solid alkali metal salt.

7. A process according to claim 6 wherein said solid alkali metal salt is potassium iodide.

8. A process according to claim 1 wherein the 2-alkylthiobenzaldehyde of general formula (I) is 2-methylthiobenzaldehyde o 2-ethylthiobenzaldehyde.

9. A process according to claim 1 wherein the halo compound of general formula (II) is chloroacetone, bromoacetone, chloroacetic acid or bromoacetic acid.

10. A process according to claim 1 wherein the 2-substituted benzo[b]thiophene of general formula (III) is 2-acetylbenzo[b]thiophene or 2-benzo[b]thiophenecarboxylic acid.

11. A process for producing an alkylthiobenzaldehyde of general formula (VI) which comprises reacting a halobenzaldehyde of general formula (IV) with an alkanethiol of general formula (V) in the presence of a base and water in a heterogeneous phase:

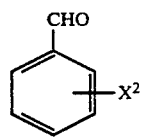  (IV)

wherein $X^2$ means Cl or Br, $R^3SH$  (V)

wherein $R^3$ means an alkyl group of 1 to 4 carbon atoms,

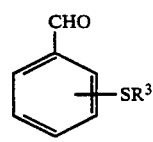  (VI)

wherein $R^3$ is as defined above.

12. A process according to claim 11 wherein the reaction is conducted in the presence of a phase transfer catalyst.

13. A process according to claim 12 wherein said phase transfer catalyst is a quaternary ammonium salt or a quaternary phosphonium salt.

14. A process according to claim 11 wherein the halobenzaldehyde of general formula (IV) is 2-chlorobenzaldehyde or 4-chlorobenzaldehyde.

15. A process according to claim 11 wherein the alkylthiobenzaldehyde of general formula (VI) is 2-methylthiobenzaldehyde, 4-methylthiobenzaldehyde, 2-ethylthiobenzaldehyde or 4-ethylthiobenzaldehyde.

16. A process according to claim 11 wherein said base is an alkali metal hydroxide.

* * * * *